United States Patent [19]

Sugai et al.

[11] Patent Number: 5,426,244
[45] Date of Patent: Jun. 20, 1995

[54] METHOD FOR PREPARING DIHYDRIC PHENOLS

[75] Inventors: Ryuji Sugai, Niigata; Osamu Kondo, Ibaragi; Yuki Motoyama; Shu Yoshida, Ibaragi, all of Japan

[73] Assignee: Mitsubishi Gas Chemical Company, Inc., Tokyo, Japan

[21] Appl. No.: 235,982

[22] Filed: May 2, 1994

Related U.S. Application Data

[63] Continuation-in-part of Ser. No. 993,623, Dec. 21, 1942, abandoned.

[30] Foreign Application Priority Data

Dec. 20, 1991 [JP] Japan .................. 3-338304
Mar. 11, 1993 [JP] Japan .................. 5-050901

[51] Int. Cl.$^6$ .................. C07C 37/60; C07C 37/00
[52] U.S. Cl. .................. 568/771; 568/741; 568/803
[58] Field of Search .............. 568/771, 733, 741, 768, 568/629, 803

[56] References Cited

U.S. PATENT DOCUMENTS 3,914,323 10/1975 Maggioni .................. 568/771
4,533,766 8/1985 Drauz et al. .................. 568/771
4,578,521 3/1986 Chang et al. .................. 568/771

FOREIGN PATENT DOCUMENTS 0132783 2/1985 European Pat. Off. ........... 568/771
0299893 1/1989 European Pat. Off. .
0314582 5/1989 European Pat. Off. .
2657340 1/1991 France .
2116974 10/1983 United Kingdom .

OTHER PUBLICATIONS

*Catalysis Letters*, vol. 1, pp. 81–84, 1988.
*Chemical Abstracts*, vol. 112, No. 24, p. 128, Jun. 11, 1990.

*Primary Examiner*—Werren B. Lone
*Attorney, Agent, or Firm*—Sughrue, Mion, Zinn, Macpeak & Seas

[57] ABSTRACT

Phenols are reacted with a hydrogen peroxide in the presence of a crystalline titanosilicate catalyst and a cyclic ether, such as dioxane, as a solvent. The method provides especially high para-selectivity compared with conventional methods, and, at the same time, provides high yields of dihydric phenols versus hydrogen peroxide.

19 Claims, No Drawings

METHOD FOR PREPARING DIHYDRIC PHENOLS

This is a continuation-in-part of U.S. patent application No. 07/993,623, filed Dec. 21, 1992, now abandoned.

BACKGROUND OF THE INVENTION

1. Field of the Invention

The present invention relates to a novel method for preparing dihydric phenols, such as hydroquinone and catechol, useful as a raw material for several industrial chemicals, pharmaceuticals, agricultural chemicals and perfumes, etc.

2. Description of the Related Art

Methods for preparing dihydric phenols, such as a hydroquinone and catechol, which are produced by oxidizing phenols with hydrogen peroxide in the presence of many catalyst systems have been studied for a long time.

For example, the following references describe the oxidation of phenols in the presence of various catalyst: Japanese Patent Publication Kokai No. 50-130727 describes phenol oxidation in the presence of ketones, such as, 4-methyl-2-pentanone and methyl phenyl ketone, etc., and sulfates, such as an aluminum sulfate;

Japanese Patent Publication Kokoku No. 56-47891 describes phenol oxidation in the presence of strong acid mineral acids, such as a perchloric acid;

U.S. Pat. No. 3,914,323 describes a method known as the Fenton Method in which phenols are oxidized in the presence of iron or cobalt salts;

U.K. Patent No. 2,116,974 and EP Patent No. 314,582 describe a method in which phenols are oxidized in the presence of synthetic zeolites containing Ti atoms as a catalyst;

EP Patent No. 299,893 describes a method in which phenols are oxidized in the presence of a lamellar acid clay as a catalyst; and EP Patent No. 132,783 describes a method in which phenols are oxidized in the presence of a strong acid type ion-exchange resin as a catalyst, etc.

All of the above methods produce a high yield of dihydric phenols versus hydrogen peroxide, but have a very serious problem i.e., for example, a hydroquinone and a catechol are co-produced when phenols are oxidized with hydrogen peroxide. That is, the para- to orth-isomer ratio (P/O) of dihydric phenols in the above cases using a ketoneperoxide catalysts system, mineral acid system and the Fenton reaction are 0.4–0.7; therefore, ortho-isomers, which are in little demand, are produced in large amounts compared with the amounts of para-isomers. For this reason, there is the drawback that the production amounts and the production costs of the para-isomers are very adversely influenced by the market for ortho-isomers, e.g., the market for catechols. EP Patent No. 314,582 discloses that an improvement of the para-selectivity can be accomplished by using a titanosilicate catalyst having the same crystalline structure as ZSM-5 zeolite; in this case, however, the P/O ratio is also around 1. In the case where lamellar clay is used (EP Patent No. 299,893), an example is set forth in which the P/O ratio was improved to 1.86; but the conversion ratio of hydrogen peroxide was small, and the method, therefore, is not practical. Further, there is a report that the P/O ratio can be improved to 12.5 when a strong acid type ion-exchange resin containing a cation of a transition metal, such as Ti or V etc., is used as a catalyst; the yield of dihydric phenols versus hydrogen peroxide was small, however, and the result, therefore, is unsatisfactory. A method of obtaining para-isomers, utilizing the shape selectivity of ZSM-5 zeolite (U.S. Pat. No. 4,578,521) has recently been disclosed. Although the present inventors tried to hydroxylate a phenol according to the method described in the above U.S. Patent, satisfactory yield and selectivity could not be obtained, and the method was not sufficiently reproducible.

SUMMARY OF THE INVENTION

The inventors of the present invention have extensively studied with the objectives of producing dihydric phenols, the two hydroxyl groups which have a para-relationship to each other, in high yields and high selectivity. They have found that the above objects of the present invention can be easily achieved by combining cyclic ethers in the reaction system in which the hydroxylation reaction of phenols by a hydrogen peroxide is carried out using a crystalline titanosilicate as a catalyst, and have thus accomplished the present invention.

The novel preparation methods of dihydric phenols according to the present invention are as follows:

a) the phenols are reacted with hydrogen peroxide in the presence of a crystalline titanosilicate and cyclic ethers;

b) preferably, said titanosilicate is a pentasyl type titanosilicate;

c) as a further preference, the cyclic ethers are ones selected from the group consisting of 1,3-dioxolane, tetrahydrofuran, tetrahydropyran, 1,3-dioxane, 1,4-dioxane and 1,3,5-trioxane;

d) the most preferred cyclic ether is 1,4-dioxane;

e) said cyclic ethers are preferably used in an amount of 0.01–1.2 moles per 1 mole of phenols;

f) more preferably, the cyclic ethers are used in an amount of 0.05–0.8 moles per 1 mole of phenols;

g) the reaction is preferably carried out in a polar solvent which contains cyclic ethers;

h) the P/O ratio is preferably controlled by varying the ratio of the amount of cyclic ether to the amount of the phenols;

i) the polar solvent is selected from the group consisting of water, acetone, methanol, acetonitrile and ethanol, and the preferred polar solvent is water;

j) the hydrogen peroxide is used in an amount of not more than 0.5, and preferably is used in an amount of not more than 0.3 moles per 1 mole of the phenols;

k) the reaction temperature is in the range of from about 50° to about 150° C.;

l) the titanosilicate catalyst is used in an amount of from about 1–20% by weight, preferably 2.5–10% by weight, per total amount of reaction mixture; and m) the phenols used in the reaction are selected from the group consisting of phenol, anisole, cresol and xylenol.

DESCRIPTION OF THE PREFERRED EMBODIMENTS

The present invention will be described below in more detail.

In the present invention, crystalline titanosilicates, the general formula of which is shown by $xTiO_2 \cdot (1-x)SiO_2$ ($0.0001 < x < 0.5$, more preferably $0.001 < x$-

<0.05), are used as catalysts. Preferably, the crystalline titanosilicate used will have a crystalline structure similar to ZSM-5; such materials are called generically "pentasyl type"; their general formulae as shown by $xTiO_2 \cdot (1-x)SiO_2$ (wherein, $0.0001 < x < 0.5$, more preferably $0.001 < x < 0.05$) are particularly preferably used.

Known methods for the preparation of the catalyst include either the method in which a reaction mixture containing a silicon source, a titanium source, nitrogen containing compounds and water is prepared; then hydrothermal synthesis is carried out, or the method in which a zeolite, such as ZSM-5, etc., is de-alumininated in the presence of chloric acid, and Ti atoms are incorporated (B. Kraushaar and J. H. C. Van Hooff, *Catl. Lett.*, 1(4), 81, (1988)), etc. In the present invention, although either method may be used, the former method is described in detail hereinafter.

As a silicon source, a tetraalkyl orthosilicate, a colloidal silica, etc., may be used. As a tetraalkyl orthosilicate, a tetraethyl orthosilicate is preferably used. As a titanium source, a tetraalkyl orthotitanate, or a hydrolytic halogenated titanium compound, such as a $TiOCl_2$ may be used. As a tetraalkyl orthotitanate, a tetraethyl orthotitanate, a tetrapropyl orthotitanate, or a tetrabutyl orthotitanate may be preferably used. As a nitrogen containing compound, a tetraalkylammonium ion, preferably a tetrapropylammonium hydroxide, or a tetrabutylammonium hydroxide may be used. Further, as a nitrogen containing compound, there may be used a titanosilicate having various crystalline forms which may be synthesized by using amines which are generally used in the preparation of a zeolite catalyst, such as a diethanolamine, a piperidine, etc.

In preparing the titanosilicate of the present invention, the molar ratio in the charge is preferably $Si/Ti=10-50$, $H_2O/Si=10-100$, and the nitrogen containing compound$/Si=0.05-1$. The crystalline titanosilicate catalyst is obtained from the reaction products obtained by mixing the above charge and subjecting the charge to hydrothermal synthesis in an autoclave at $100°-220°$ C. for 1-1000 hours; the thus obtained solid is washed with ion-exchanged water, dried, and calcined in air at $400°-600°$ C. for 1-10 hours.

In the case when a tetrapropylammonium hydroxide is used as the nitrogen-containing compound, a titanosilicate having a silicalite-1 type structure (abbreviated as TS-1) is obtained (Japanese Patent Publication Kokoku No. 1-42889), and in the case when a tetrabutylammonium hydroxide is used, a titanosilicate having a silicalite-2 type structure (abbreviated as TS-2) is obtained (J. S. Reddy et al., *Appl. Catal.*, 5 8(2), L1-L4, (1990)). The amount of the titanosilicate catalyst used is in the range of 1-20% by weight, preferably 2.5-10% by weight, per total amount of reaction mixture. When a smaller amount is used, the reaction rate is slower; and when a larger amount is used, it is not economical. So, the above range is the most practical range to use.

As the phenol used in the present invention, a phenol, an anisole, a cresol and a xylenol are preferably used; phenol is especially preferred.

The concentration of hydrogen peroxide is not critical; however, a 30-60 weight % aqueous solution, which is readily commercially available, is preferably used.

The amount of hydrogen peroxide is preferably not more than 0.5 moles, and more preferably, is not more than 0.3 moles per 1 mole of the phenol, in order to avoid contributing to the side reaction. The whole quantity of hydrogen peroxide may be added at once, but, it is preferable to add it intermittently or continuously in order to inhibit the formation of excess heat and the undesired side reaction.

As described above, a characteristic of the preparation method of the present invention is that cyclic ethers are also present when the phenol is hydroxylated in the presence of a crystalline titanosilicate as a catalyst. As the cyclic ether, a 1,3-dioxane, a 1,4-dioxane, a 1,3,5-trioxane, etc., are exemplified. Among those, the 1,4-dioxane is especially preferred.

The amount of the cyclic ether used is in the range of 0.01-1.2 moles per 1 mole of phenol, and preferably, in the range from 0.05 to 0.8. In the case where an amount less than the stated range is used, a sufficient addition effect is not achieved, and then the P/O ratio becomes small. On the other hand, in the case where more cyclic ether is used than the stated range, the yield of the dihydric phenol decreases, which is not desirable. Further, it is possible to control the P/O ratio within a certain range by varying the ratio of the cyclic ether and phenol which is used.

The reaction temperature may be in the range from $50°$ to $150°$ C., and preferably, in the range from $60°$ to $120°$ C. When the temperature is lower than the stated range, the reaction rate becomes too slow; on the other hand, when the temperature is higher than the stated range, decomposition of the hydrogen peroxide or the by-production of a high boiling material increases, and the yield of dihydric phenol decreases. These results are undesirable.

Although the cyclic ether itself can be used as a solvent in the reaction of the present invention, it is preferable that a solvent other than the cyclic ether also be used in combination with the cyclic ether. As the other solvent, a polar solvent, such as methanol, ethanol, acetonitrile, acetone and water etc., may be used. Among these, water is especially preferable. The amount of the co-solvent used is not critical, but, when used in excess, the concentration of the reactant decreases, and then the reaction rate decreases; it is preferable, therefore, that the amount of the co-solvent used is within 1 times by weight of the phenols.

The method of the present invention can be carried out as either a batch or continuous process.

In a continuous reaction method, the upper limit of the conversion ratio of the phenol is determined by the ratio of hydrogen peroxide feed against phenol feed ($H_2O_2$/PhOH). At the time of feed, the mole ratio of hydrogen peroxide against phenol is preferably 0.3 and less, more preferably 0.2 and less. When the mole ratio of hydrogen peroxide against phenol is too large, the yield of the dihydric phenol is decreased by a side reaction.

The hydrogen peroxide feed is preferably diluted to proper concentration with a solvent. As the solvent, a polar solvent, such as water, methanol, ethanol, acetonitrile, and acetone, can be used. Among these polar solvents, water is particularly preferred. The concentration of the hydrogen peroxide determines the steady-state concentration of hydrogen peroxide and solvent in the reaction solution.

The steady-state concentration of the solvent, especially water, influences the yield of the dihydric phenol. When the steady-state concentration of the water is too small, the yield of the dihydric phenol is decreased. When the steady-state concentration of water is too large, the concentration of the dihydric phenol in the product becomes small, and requires the costly steps of separation and purification, and therefore it is not desirable. Thus, in order to improve the yield of the dihydric phenol and minimize the cost of separation and purification, the steady-state concentration of water in the reaction system is preferably within the range of from 50 to 80 mole %.

The concentration of the hydrogen peroxide that satisfies the above condition of a steady-state concentration of water is no more than 20% by weight, and preferably no more than 10% by weight.

One important factor in determining the conversion ratio of the hydrogen peroxide is the average residence time, which is determined by the feed rate of all the reactants and the volume of the reaction mixture. In the present invention, the average residence time is determined in relation with the above-mentioned factors. In that case, the steady-state concentration of the hydrogen peroxide in the reaction system is preferably close to zero. That is, the steady-state concentration of the hydrogen peroxide is preferably 0.001% to 0.5% by weight, more preferably 0.005% to 0.3% by weight, most preferably 0.01% to 0.1% by weight, in the reaction mixture.

The range of the average residence time is preferably from 0.5 to 3 hours, more preferably, from 1 to 2 hours. When the average residence time is too short, the steady-state concentration of the hydrogen peroxide increases, and the yield extremely decreases by the contribution of side reactions. When the average residence time is too long, the effect of continuous reaction becomes too small, and the effect of preventing the cyclic ether from decreasing is lowered. The continuous method is carried out either in a continuous stirred tank reactor or in a fixed bed reactor, more preferably in a continuous stirred tank reactor.

The present invention provides a method for the preparation of dihydric phenols which is characterized in that the phenols are reacted with a hydrogen peroxide using a crystalline titanosilicate catalyst in the presence of a cyclic ether, and provides especially high para-selectivity compared with conventional methods, while at the same time, providing a high yield of dihydric phenols versus hydrogen peroxide. Therefore, the present method is believed to have industrially important significance.

EXAMPLES

Hereinafter, the method of the present invention is described in more concrete terms. The following examples, however, do not limit the method of the present invention. Further, the degree of conversion of hydrogen peroxide, and the yield of dihydric phenols which appear in the following examples and comparative examples are defined by the following formulas:

the degree of conversion of hydrogen peroxide
(%)=[(number of moles of a hydrogen peroxide supplied)−(number of moles of a hydrogen peroxide unreacted)]÷(number of moles of a hydrogen peroxide supplied)×100 the yield of dihydric phenols (%)=[(number of moles of dihydric phenols produced)÷(number of moles of hydrogen peroxide converted)]×100

Preparation of the Catalyst

TS-1 Catalyst

Into a flask having an internal volume of 200 ml and having four inlets, 45.5 g of a tetraethyl orthosilicate and 1.5 g of a tetraethyl orthotitanate were added under nitrogen flow, and dissolved homogeneously with stirring in an ice bath. Thereafter, 100 g of a 20% solution of a tetrapropyl-ammonium hydroxide was added dropwise, carefully using a dropping funnel, the mixture rose gradually in temperature to room temperature, with stirring for 1 hour. The resulting colorless and homogeneous solution was heated to 80° C. in an oil bath, and stirred for 5 hours, while removing ethanol formed by hydrolysis. After the termination of the hydrolysis, 60 ml of ion-exchanged water was added into the reaction mixture; thus the volume of the mixture was brought up to 150 ml. Next, the reaction mixture was charged into a 300 ml stainless steel autoclave, hydrothermally synthesized at 175° C., under its own pressure for 10 days. The thus formed white crystals were removed by centrifugation from the mother liquor, washed sufficiently with ion-exchanged water, then dried at 90° C. for 6 hours. After drying sufficiently, the crystals were heat-treated in air at 550° C. for 6 hours, crystalline titanosilicate was obtained (hereinafter referred to as TS-1). The X-ray diffraction and infrared spectrum of the recovered crystals were the same as are described in Japanese Patent Publication Kokoku No. 1-42889.

TS-2 Catalyst

Into a four-necked flask having an internal volume of 200 ml, 45 g of a tetraethyl orthosilicate was charged under nitrogen flow, and a mixture of 64 g of a solution of 1 mole/l of tetrabutyl ammonium hydroxide in methanol and 30 g of ion-exchanged water was added dropwise with sufficient stirring in an ice bath. After the addition, a dry 2-propanol (10 g) solution of a tetrabutyl orthotitanate (2.23 g) was added dropwise with sufficient stirring in an ice bath.

To the thus obtained solution was added 50 g of ion-exchanged water, and the solution was heated to 80° C. in an oil bath, stirred for 3 hours, while removing ethanol and butanol, which were formed by hydrolysis, and the added 2-propanol. 50 g of ion-exchanged water was added into the reaction mixture; then the total volume of the mixture was brought up to 125 ml. Next, the reaction mixture was charged into a 300 ml stainless steel autoclave, hydrothermally synthesized at 170° C., under its own pressure for 10 days. After the hydrothermal synthesis, the same procedure, as was used to obtain the TS-1 catalyst, was used to obtain the crystalline titanosilicate, hereinafter referred to as TS-2. The X-ray diffraction and infrared spectrum of the recovered crystals were the same as the spectrum reported in J. D. Reddy.

EXAMPLE 1

A stirrer, a cooler and a temperature indicator were provided to a four-necked flask having an internal volume of 200 ml; to this flask, 13.0 g of phenol, 4.0 g of 1,4-dioxane, 6.0 g of water and 1.3 g of TS-1 catalyst, prepared according to the above described procedure, were added, and heated to 70° C. by an oil bath. After the temperature of the mixture reached 70° C., 3.0 g of 31 weight % of hydrogen peroxide was added dropwise using a quantitative pump over 2 hours, and stirred further for 20 minutes after the addition. The reaction solution was analyzed by liquid chromatography, and the yields of hydroquinone and catechol were calculated. The results are shown in Table 1.

catalyst, 5.0 g of 1,4-dioxane, and 5.0 g of water were used. The results are shown in Table 1.

TABLE 1

| | Catalyst Added (g) | Cyclic Ether | Solvent | Amount added (g) Cyclic Ether | Solvent | Degree of Conversion of Hydrogen Peroxide (%) | DHB Yield (%) | P/O Molar Ratio |
|---|---|---|---|---|---|---|---|---|
| Ex. 1 | 1.3 | 1,4-dioxane | water | 4 | 6 | 100 | 75 | 7.3 |
| Ex. 2 | 1.3 | 1,4-dioxane | water | 2 | 8 | 100 | 79 | 4.0 |
| Ex. 3 | 0.6 | 1,4-dioxane | — | 10 | 0 | 100 | 43 | 4.4 |
| Ex. 4 | 0.6 | 1,4-dioxane | — | 5 | 0 | 100 | 57 | 5.3 |
| Ex. 5 | 0.6 | 1,4-dioxane | — | 2 | 0 | 100 | 46 | 1.9 |
| Ex. 6 | 0.6 | 1,4-dioxane | water | 5 | 5 | 100 | 71 | 6.9 |
| Ex. 7 | 0.6 | 1,4-dioxane | water | 2 | 8 | 100 | 75 | 4.4 |
| Ex. 8 | 0.6 | 1,4-dioxane | water | 0.5 | 9.5 | 100 | 67 | 2.0 |
| Ex. 9 | 5.2 | 1,4-dioxane | water | 5 | 5 | 100 | 70 | 5.4 |
| Ex. 10 | 0.6 | tetrahydropyran | water | 5 | 5 | 73 | 33 | 2.0 |
| Ex. 11 | 0.6 | tetrahydrofuran | — | 10 | 0 | 100 | 6 | 5.0 |
| Ex. 12 | 0.6 | tetrahydrofuran | water | 2 | 8 | 100 | 25 | 3.2 |
| Ex. 13 | 0.6 | 1,3-dioxane | water | 5 | 5 | 100 | 63 | 1.9 |
| Ex. 14 | 0.6 | 1,4-dioxane | acetone | 5 | 5 | 100 | 43 | 2.5 |
| Ex. 15 | 0.6 | 1,4-dioxane | methanol | 5 | 5 | 100 | 45 | 6.5 |
| Ex. 16 | 0.6 | 1,4-dioxane | acetonitrile | 5 | 5 | 100 | 33 | 2.7 |
| Ex. 17 | 0.6 | 1,4-dioxane | water | 5 | 5 | 100 | 45 | 4.6 |
| Ex. 18 | 0.6 | 1,4-dioxane | water | 5 | 5 | 82 | 9 | 11.0 |
| Com. Ex 1 | 1.3 | none | water | 0 | 6 | 100 | 77 | 1.2 |

Note: DHB = diphenols

EXAMPLE 2

The same procedure was used as in Example 1, except that 2.0 g of 1,4-dioxane, and 8.0 g of water were used instead of 4.0 g of 1,4-dioxane, and 6.0 of water as in Example 1. The results are shown in Table 1.

COMPARATIVE EXAMPLE 1

The same procedure was used as in Example 1, except that 4.0 g of 1,4-dioxane was not added in Example 1. The results are shown in Table 1.

EXAMPLES 3-9

The same procedure was used in Example 1, except that 1,4-dioxane, water, and TS-1 catalyst were used respectively in the amounts as described in Table 1. The results are shown in Table 1.

EXAMPLES 10-13

The same procedure as in Example 1 was used, except that 0.6 g of TS-1 catalyst was used; further the amount of water added and the kind of cyclic ether used were changed as described in Table 1. The results are shown in Table 1.

EXAMPLES 14-16

The same procedure was used as in Example 1, except that 0.6 g of TS-1 catalyst, 5.0 g of 1,4-dioxane and 5.0 g of solvent were used as described in Table 1, instead of the 1.3 g of TS-1 catalyst, 4.0 g of 1,4-dioxane, and 6.0 g of water as were used in Example 1. The results are shown in Table 1.

EXAMPLE 17

The same procedure was used as in Example 1, except that 0.6 g of the TS-1 catalyst, prepared according to the above procedure was used instead of the 1.3 g of TS-1 catalyst as was used in Example 1. The results are shown in Table 1.

EXAMPLE 18

The same procedure was used in Example 1, except that 14.8 g of anisole was used instead of the 13 g of phenol as was used in Example 1; also 0.6 g of TS-1

EXAMPLE 19

Into a flask having an internal volume of 100 ml and having a reflux condenser, a temperature indicator and a stirrer, 2.5 g of TS-1 catalyst prepared according to the above described procedure was added, and 5% by weight hydrogen peroxide aqueous solution was introduced using a supply pump at a feed rate of 10 ml/h. A mixture of phenol containing 15 mole % of 1,4-dioxane (DOX) was also introduced using another supply pump at a feed rate of 20 ml/h.

When the volume of the reaction mixture became 50 ml, an exhaust pump was started. The volume of the reaction mixture was made constant by exhausting the reaction mixture at an exhaust rate of 30 ml/h. At this point, the average residence time was 1.5 hours.

The flask was heated using an oil bath, and the reaction temperature maintained at 80° C. After the reaction reached a steady-state, the amount of each component in the reaction mixture which was exhausted by the exhaust pump in a unit of time was determined by liquid chromatography and gas chromatography, and the yield, conversion ratio etc., were calculated according to the following formulae. The results are shown in the Table 2.

DHB Yield (%) =

$$\frac{\text{Production amount of dihydric phenol(mole/}h\text{)}}{\text{Supply amount of hydrogen peroxide(mole/}h\text{)} - \text{Exhaust amount of hydrogen peroxide (mole/}h\text{)}} \times 100$$

DOX Reduction (%) =

$$\frac{\text{Supply amount of } DOX\text{(mole/}h\text{)} - \text{Exhaust amount of } DOX\text{(mole/}h\text{)}}{\text{Supply amount of hydrogen peroxide(mole/}h\text{)} - \text{Exhaust amount of hydrogen peroxide(mole/}h\text{)}} \times 100$$

Conversion rate of PhOH (%) = $\frac{\text{Supply amount of PhOH(mole/}h\text{)} - \text{Exhaust amount of PhOH(mole/}h\text{)}}{\text{Supply amount of PhOH(mole/}h\text{)}} \times 100$ PhOH Selectivity (%) =

-continued dioxane was decreased by 9% based on the hydrogen peroxide reacted.

TABLE 2

| EX/ Com. EX | Conc. of H$_2$O$_2$ (wt %) | Residence Time (h) | Unreacted H$_2$O$_2$ (%) | Yield of DHB (%) | Reduction of DOX (%) | Conversion Rate of PhOH (%) | Selectivity of PhOH (%) | HQ/CT |
|---|---|---|---|---|---|---|---|---|
| Ex. 19 | 5.0 | 1.5 | 0.0 | 80 | 0 | 10 | 81 | 4.8 |
| Ex. 20 | 10.0 | 1.5 | 0.0 | 68 | 0 | 19 | 69 | 4.4 |
| Com. Ex. 2 | 31.0 | — | 0.0 | 75 | 15 | 25 | 90 | 5.0 |
| Com. Ex. 3 | 31.0 | 1.5 | 69.0 | 17 | 3.2 | 40 | 45 | 1.4 |
| Com. Ex. 4 | 10.0 | 0.6 | 55.0 | 40 | 9.0 | 8 | 40 | 2.1 |

$$\frac{\text{Production amount of dihydric phenol(mole/h)}}{\text{Supply amount of PhOH(mole/h)} - \text{Exhaust amount of PhOH(mole/h)}} \times 100$$

$$HQ/CT = \frac{\text{Production amount of hydroquinone(mole/h)}}{\text{Production amount of cathecol(mole/h)}} \times 100$$

EXAMPLE 20

The same procedure was used as in Example 19, except that the concentration of the hydrogen peroxide feed was changed to 10% by weight. The results are shown in Table 2.

Although the yield of dihydric phenol decreased a little, 1,4-dioxane was not decreased at all.

COMPARATIVE EXAMPLE 2

25 g of phenol, 4 g of 1,4-dioxane and 15 g of water were charged into 100ml of flask, so as to be the same mole ratio as each gradient in steady condition of Example 1. In addition 0.6 g of TS-1 was added, and the mixture was heated to 80° C. using an oil bath.

In a semi-batch reaction, 7.3 g of 31% by weight hydrogen peroxide was added dropwise over 5 hours with stirring using a feed pump. After an additional 1 hour of stirring after completing the feed, the reaction mixture was analyzed, and the results obtained are shown in Table 2. As clearly seen from these results, 1,4-dioxane decreased by 15 mole % based on hydrogen peroxide.

COMPARATIVE EXAMPLE 3

The same procedure was used as in Example 19, except that the concentration of the hydrogen peroxide feed was changed to 31% by weight. The results are shown in Table 2. Under this condition, the percentage of the unreacted hydrogen peroxide was very high, i.e., 69%, and the yield of dihydric phenol was very small, and paraselectivity decreased.

COMPARATIVE EXAMPLE 4

The same procedure was used as in Comparative Example 3, except that the amount of the TS-1 catalyst was changed to 1.5 g, and the average residence time was changed to 0.6 hours. The results are shown in Table 2. Due to these changes, the percentage of the unreacted hydrogen peroxide was high, i.e., 55%, and as the result, the yield of dihydric phenol was 40%, the HQ/CT ratio became worse, i.e., 2.1, and further, 1,4-dioxane was decreased by 9% based on the hydrogen peroxide reacted.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefor intended to be embraced therein.

What is claimed is:

1. A method for preparing dihydric phenols comprising reacting a phenol with hydrogen peroxide under suitable conditions to produce said dihydric phenols wherein said reaction is carried out in the co-presence of a crystalline titanosilicate catalyst and a cyclic ether.

2. The method according to claim 1, wherein said titanosilicate catalyst is a pentasyl type titanosilicate.

3. The method according to claim 1, wherein said cyclic ether is selected from the group consisting of 1,3-dioxolane, tetrahydrofuran, tetrahydropyran, 1,3-dioxane, 1,4-dioxane and 1,3,5-trioxane.

4. The method according to claim 1, wherein said cyclic ether is 1,4-dioxane.

5. The method according to claim 1, wherein said cyclic ether is used in an amount of from about 0.01 to about 1.2 moles per 1 mole of phenol.

6. The method according to claim 1, wherein said cyclic ether is used in an amount of from about 0.05-0.8 moles per mole of phenol.

7. The method according to claim 1, which is characterized in that the reaction is carried out in a polar solvent which contains a cyclic ether.

8. The method according to claim 4, which is characterized in that the para- to ortho-isomer P/O ratio (P/O) is controlled by varying the ration of the cyclic ether to the phenols.

9. The method according to claim 7, wherein said polar solvent is selected from the group consisting of water, acetone, methanol, acetonitrile and ethanol.

10. The method according to claim 7, wherein said polar solvent is water.

11. The method according to claim 1, wherein said hydrogen peroxide is used in an amount of not more than about 0.5 moles per 1 mole of the phenol.

12. The method according to claim 1, wherein said hydrogen peroxide is used in an amount of not more than about 0.3 moles per 1 mole of the phenol.

13. The method according to claim 1, wherein the reaction temperature is in the range of from about 50° to about 150° C.

14. The method according to claim 1, wherein said titanosilicate catalyst is used in an amount of from about 1–20% by weight, per total amount of reaction mixture.

15. The method according to claim 1, wherein said titanosilicate catalyst is used in an amount of from about 2.5–10% by weight, per total amount of reaction mixture.

16. The method according to claim 1, wherein said phenol is selected from the group consisting of phenol, anisole, cresol and xylenol.

17. A method for preparing dihydric phenols comprising reacting a phenol with hydrogen peroxide in the presence of a crystalline titanosilicate and cyclic ethers, wherein said method is a continuous process in which the hydrogen peroxide concentration in the reaction mixture is kept constant.

18. The method according to claim 17, wherein the hydrogen peroxide concentration in reaction mixture is from 0.001% to 0.5% by weight.

19. The method according to claim 16, wherein said phenol is phenol or anisole.

* * * * *